United States Patent
Phillips et al.

[11] Patent Number: 5,256,537
[45] Date of Patent: Oct. 26, 1993

[54] CULTURETTE SAFETY SLEEVE

[75] Inventors: Robert E. Phillips, Studio City, Calif.; David M. Mathis, El Paso, Tex.; Ray Edwards, Jr., El Paso, Tex.; Albert Lopez, El Paso, Tex.

[73] Assignee: Becton, Dickinson and Company, Franklin Lakes, N.J.

[21] Appl. No.: 806,940

[22] Filed: Dec. 11, 1991

[51] Int. Cl.$^5$ ............................................ G01N 33/569
[52] U.S. Cl. ........................... 435/7.1; 128/759; 128/760; 128/763; 128/771; 222/80; 222/83.5; 422/58; 422/61; 422/101; 435/7.2; 435/294; 435/295; 435/296; 435/29; 435/30; 436/805; 436/807; 436/810
[58] Field of Search .............. 422/58, 61, 101; 435/244–246, 7.1, 7.2, 29, 30, 34; 128/759, 760, 763, 771; 436/805, 807, 810; 222/80, 82.5, 187

[56] References Cited

U.S. PATENT DOCUMENTS

| | | | |
|---|---|---|---|
| 1,379,608 | 5/1921 | Bailey | 15/429 |
| 2,528,709 | 11/1950 | Raymond et al. | 15/424 |
| 3,163,160 | 12/1964 | Cohen | 435/295 |
| 3,513,830 | 5/1970 | Kalayjian | 128/759 |
| 3,954,563 | 5/1976 | Mennen | 435/295 |
| 3,954,564 | 5/1976 | Mennen | 435/295 |
| 4,014,748 | 3/1977 | Spinner et al. | 435/296 |
| 4,018,653 | 4/1977 | Mennen | 435/295 |
| 4,184,483 | 1/1980 | Greenspan | 435/245 |
| 4,196,167 | 4/1980 | Olsen | 128/759 |
| 4,206,843 | 6/1980 | Rainey | 435/295 |
| 4,223,093 | 9/1980 | Newman et al. | 435/295 |
| 4,312,950 | 1/1982 | Snyder et al. | 435/295 |
| 4,586,604 | 5/1986 | Alter | 435/295 |
| 4,604,360 | 8/1986 | Hounsell | 435/295 |
| 4,653,510 | 3/1987 | Koll | 435/295 |
| 4,707,450 | 11/1987 | Nason | 435/295 |
| 4,749,655 | 6/1988 | Monthony et al. | 435/295 |
| 4,770,853 | 9/1988 | Bernstein | 435/295 |
| 4,903,708 | 2/1990 | Saint-Amund | 435/296 |
| 4,978,504 | 12/1990 | Nason | 422/58 |
| 5,078,968 | 1/1992 | Nason | 422/58 |

Primary Examiner—David Saunders
Assistant Examiner—Christopher L. Chin
Attorney, Agent, or Firm—Nanette S. Thomas

[57] ABSTRACT

The present invention is a device and method for collecting and transporting biological specimens. The device provides an environment for maintaining substantial validity of a specimen during transport. The device comprises a tubular housing with an ampoule containing medium, a specimen collector and a sleeve positioned over the tubular housing. The sleeve is used to effectively break the ampoule so as to release medium into the tubular housing so as to keep a specimen substantially viable during transport.

8 Claims, 4 Drawing Sheets

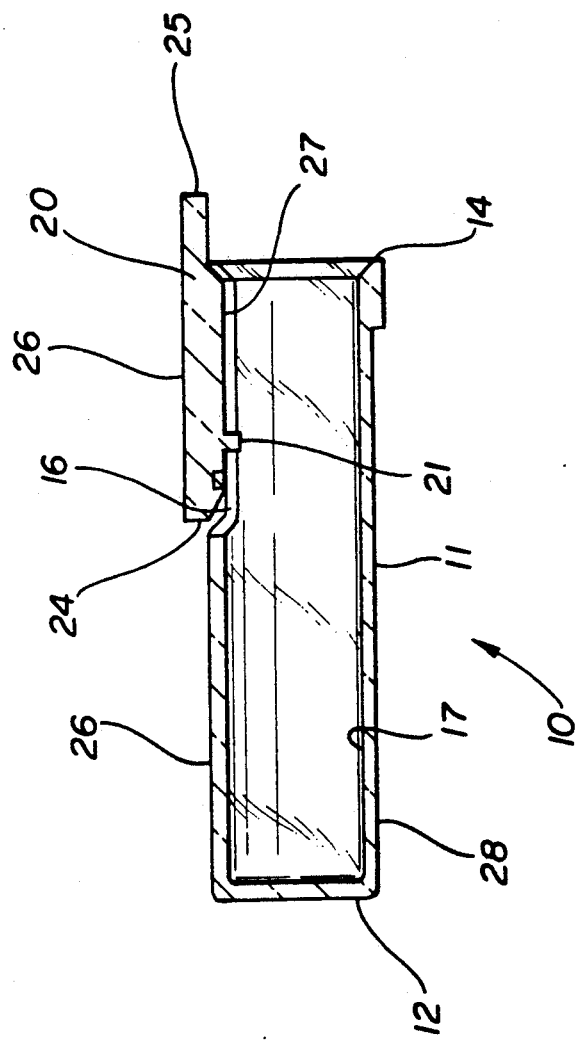

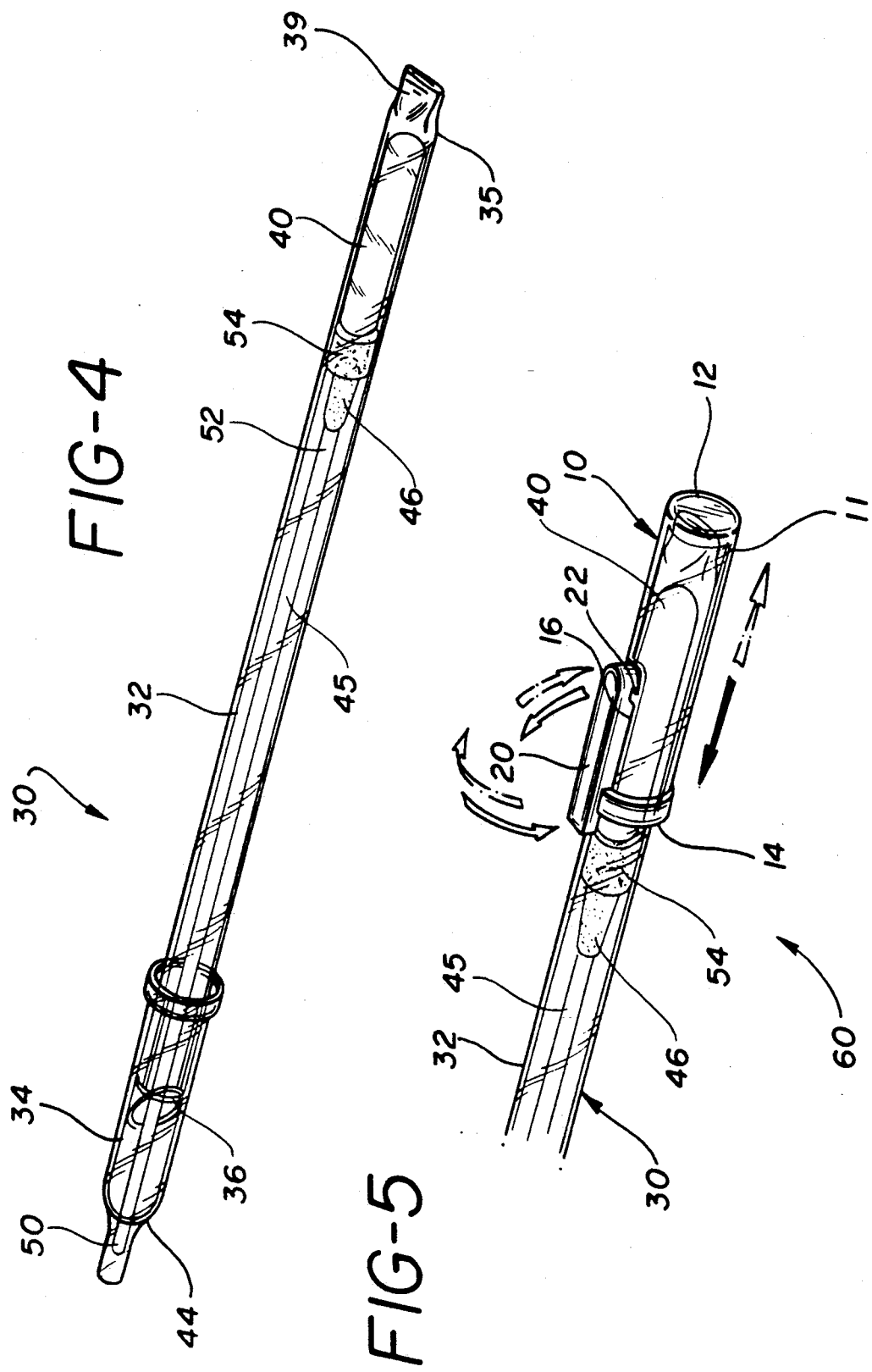

CULTURETTE SAFETY SLEEVE

BACKGROUND OF THE INVENTION

1. Field of the Invention

This invention relates to a sleeve for use with a device for collecting and transporting biological specimens.

2. Description of Related Art

An element common to most devices for collecting and transporting biological specimens in a glass ampoule in the container that can be broken to release medium into the container to keep the swab and sample moist. A typical collecting and transporting device has been described in several publications and most specifically in U.S. Pat. No. 4,014,748.

A commercially available device for collecting and transporting biological specimens is the CULTURETTE® Collection and Transport System (trademark of Becton, Dickinson and Company) sold by Becton Dickinson Microbiology Systems, Cockeysville, Md. The CULTURETTE device is for collecting and transporting a biological sample with a protective sleeve or skirt to sleeve the container where the ampoule, which is to be broken for use, is contained.

In taking a culture specimen, a collection and transport device should be constructed so that the specimen collector, e.g. swab, is maintained in a sterile environment and can be handled in an aseptic manner after the specimen of the microorganism has been taken Thereafter, the collection and transport device should be capable of furnishing a medium for the specimen microorganisms so that their viability may be maintained until such time as adequate laboratory tests may be made. Thus, a collection and transport device should be sterile before a test specimen is introduced, should have a microorganism sustaining fluid or medium for the transporting phase and should be capable of maintaining specimen integrity so as to provide accurate test results. Additionally, because millions of cultures are taken annually, the devices should be economically and feasibly manufactured and should be of relative low cost because of their single use character.

A problem which has confronted users of collection and transport devices is maintaining the viability of any microorganism which is collected. In spite of the use of a high level of skill and care in collecting the specimen so as to prevent contamination of the specimen, viability of the microorganisms is not always assured by the use of the prior art collection devices.

With the increased emphasis on the efficacy of medical products, a need exists for an improved collection and transport device which comprises a method and apparatus for effectively and efficiently handling the glass ampoule in the collection device. The improved device would better protect the specimen during handling and use. Such an improved device would also be comparatively simple and inexpensive to manufacture as compared to available devices.

SUMMARY OF THE INVENTION

The present invention is a sleeve for use with a device for collecting and transporting biological specimens. The sleeve substantially prevents the specimen collected in the device from being exposed to the outside environment.

The sleeve preferably comprises a longitudinally extended tubular body member and a lever. This sleeve may be permanently affixed to a collection device or, in an alternate embodiment, be removably disposed on the collection device and have the capability to be reused on another collection device.

The sleeve is preferably used with a collection device which comprises a tubular housing, a specimen collector and a frangible ampoule. The frangible ampoule holds and then releases medium within the tubular housing.

Most preferably, the sleeve encompasses the bottom of the collection device wherein the frangible ampoule of the collection device is housed. The lever is movable to provide appropriate pressure to the collection device to break the ampoule.

To collect and transport a specimen, the specimen collector is removed from the tubular housing. A site, such as the area of the throat, nose, ears, mouth, wound or operative sites, urogenital orifices, rectum and other sites, is sampled by contacting the site with the swab of the specimen collector. The specimen is removed from the site with the swab. Thereafter the specimen collector is preferably returned to the tubular housing with the swab being preferably positioned in contact with a swatch or pledget. The sleeve is then used to break the ampoule so that medium is released from the broken frangible ampoule.

The sleeve is disposable, or may be reusable and is preferably made of an optically clear plastic but may also be made of an opaque plastic.

The sleeve of the present invention improves the standard collection type device in that microorganisms that are obtained by the collection device may remain substantially viable through the entire specimen collection, transport, storage and identification phases.

DESCRIPTION OF THE DRAWINGS

FIG. 3A is a cross sectional view of FIG. 1 taken along line 3—3 showing an optional projection on the lever.

FIG. 4 is a perspective view illustrating a device for collecting and transporting specimens.

FIG. 5 is a partially enlarged perspective view illustrating the device for collecting and transporting specimens of FIG. 4 with the sleeve of FIG. 1.

DETAILED DESCRIPTION

Figure 1:
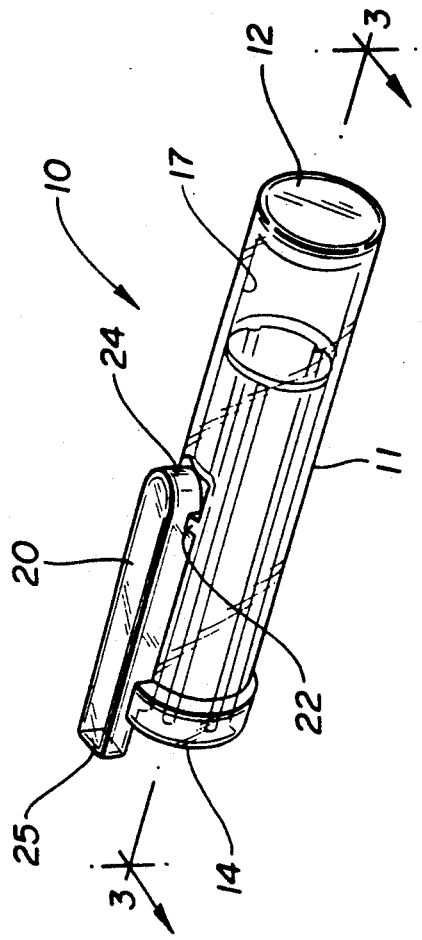
FIG. 1 is a perspective view of the sleeve.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 3:
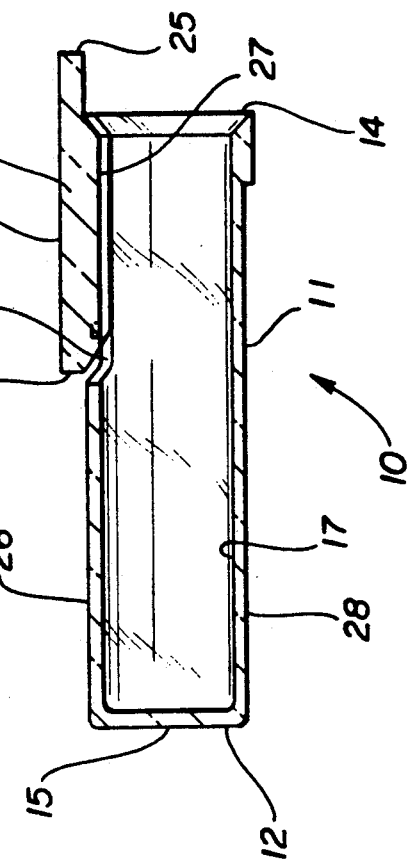
FIG. 3 is a cross sectional view of FIG. 1 taken along line 3—3.
Figure 2:
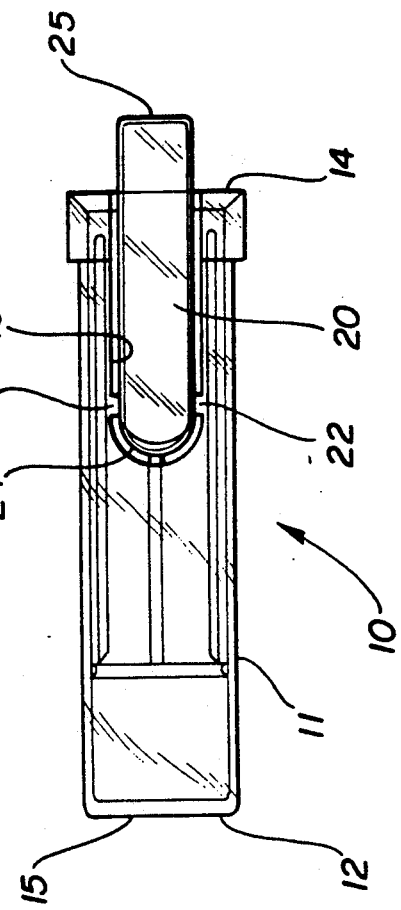
FIG. 2 is a top view of FIG. 1.

The preferred sleeve is illustrated in FIGS. 1–3 wherein sleeve 10 comprises a longitudinally extended tubular body member 11 and a lever 20 which is movable.

Tubular member 11 has a closed end extremity 12, an opposite open end extremity 14, a top side 26, a bottom side 28 and a slot 16 on the top side near the open end extremity.

The sleeve is sealed at closed end extremity 12, leaving surface 15 to which may be affixed by heat stamp, imprinting or other means a lot number or identification to enable traceability throughout the life of the sleeve.

Lever 20 is within slot 16 and is connected to tubular member 11 by at least one flexible connection 22. Lever 20 comprises a rearward end 24, a forward end 25 and a lower surface 27. Lever 20 is connected to the tubular member in such a way that it can be moved in a substantially vertical up or down direction, when oriented as shown in FIGS. 1-3.

Lever 20 may optionally be positioned as a second class lever with a projection 21 located on lower surface 27 near flexible connector 22 as shown in FIG. 3A.

The sleeve may be made of plastic or other flexible material. The sleeve is desirably opaque and most preferably translucent.

A typical collection device is illustrated in FIG. 4 wherein device 30 comprises a longitudinally extended tubular housing 32 and a specimen collector 34.

Tubular housing 32 has a closed end extremity 35 and an opposite open end extremity 36. The tubular housing is sealed at closed end extremity 35, leaving surface 39 to which may be affixed by heat stamp, imprinting or other means a lot number or identification to enable traceability throughout the life of device 30.

Disposed within the tubular housing and adjacent the closed end extremity is a substantially cylindrically shaped, sealed frangible ampoule 40. The frangible ampoule preferably holds liquid medium which may be released inside the tubular housing. The liquid in the ampoule may be a transport medium which provides an environment in which the specimen can remain substantially viable.

Frangible ampoule 40 is preferably made of, but not limited to, glass or some other frangible or rupturable material which is substantially non reactive with the liquid therein. The frangible ampoule may be ruptured or broken upon application of pressure to the outer surface of the tubular housing section containing the frangible ampoule. In this way the frangible ampoule may be opened and the liquid therein freed. A frangible ampoule made of glass is most preferred because it can be easily and effectively sterilized by autoclaving and it does not react either with the medium and/or the specimen collected.

The liquid in the ampoule may be various well known liquid media. The particular medium used is chosen on the basis of the particular type of culture to be preserved in the specimen collected. A liquid medium such as Stuart's Modified Media or a liquid culture of bile, blood or egg may be used. Gel type media may also be used.

The tubular housing may be an optically clear plastic at the open end extremity and an opaque plastic in the area enclosing the frangible ampoule. The colored plastic highlights where the frangible ampoule is located or the type of medium enclosed in the ampoule.

Preferably, the tubular housing is made of easily compressible material so that the frangible ampoule, if employed in the device, may be crushed simply by applying pressure to the tubular housing.

Specimen collector 34 comprises a cap 44, a shaft 45, and a swab 46. Cap 44 is preferably removably attachable to the open end extremity of the tubular housing. The cap is preferably adapted to telescope snugly, but slidably, over the open end extremity of the tubular housing before and after swab 46 is used.

Shaft 45 comprises a first end 50 and a second end 52. First end 50 is preferably connected to the cap and second end 52 is preferably connected to swab 46.

Swab 46 is preferably made from soft and absorbent materials including but not limited to suitable fibrous material such as cotton, polyester fibers or the like.

In order to facilitate assembly of the device, frangible ampoule 40 fits rather loosely within the tubular housing adjacent the closed extremity. To retain the loose frangible ampoule in this position and also to restrain flow of released liquid, an absorbent plug 54 is located within the tubular housing. The absorbent plug may be tightly telescoped within the tubular housing and preferably abuts the frangible ampoule to prevent the latter from sliding.

Absorbent plug 54 may be made of cotton like material or any other suitable material having absorbing properties, for properly restraining flow and/or fragments or particulate matter.

The swab is also preferably in contact with the absorbent plug and thus, as liquid is released from the frangible ampoule, the absorbent plug is moistened and in turn conducts the moisture to the swab. In addition, the absorbent plug may substantially prevent fragments of the frangible ampoule from collecting on the swab after the frangible ampoule has been broken.

In some cases, the absorbent plug may not be employed in the tubular housing, however, it is a preferred element, especially when the liquid in the ampoule has a low viscosity or is very thin or fluid. When the liquid is very fluid, the metering effect of the absorbent plug prevents the liquid and portions of the specimen from spreading onto the shaft or onto the interior face of the cap and thus prevents contamination of these parts.

The absorbent plug preferably absorbs the liquid released from the frangible ampoule and distributes the liquid to the swab, while protecting the specimen on the swab from the fragments of the broken frangible ampoule. The liquid provides a moist environment for the specimen on the swab, to keep the specimen substantially viable during transport and to prevent dehydration of the specimen.

As shown in FIG. 5, sleeve 10 is removably attached to collection device 30 at and around the closed end extremity of the device where the frangible ampoule is housed so as to form a collecting and transporting system 60.

To collect a specimen, cap 44 is removed from tubular housing 32 and swab 46 is pulled out of the tubular housing. A particular body passage of the patient then is swabbed with swab 46 to obtain a specimen. Thereafter, the swab with the specimen is returned to the tubular member with the swab being positioned in contact with absorbent plug 54. Cover 10 is then positioned at the section of the tubular housing adjacent the closed end extremity, which encloses frangible ampoule 40. The lever on the sleeve is pushed or pulled to effect a force on the tubular housing which in turn effects a force on the ampoule so that the ampoule breaks and liquid is released therein. The liquid moistens the absorbent plug which, in turn, moistens the swab to keep the specimen in suitable condition until it reaches for example, a laboratory or related facility for testing.

Figure 6:
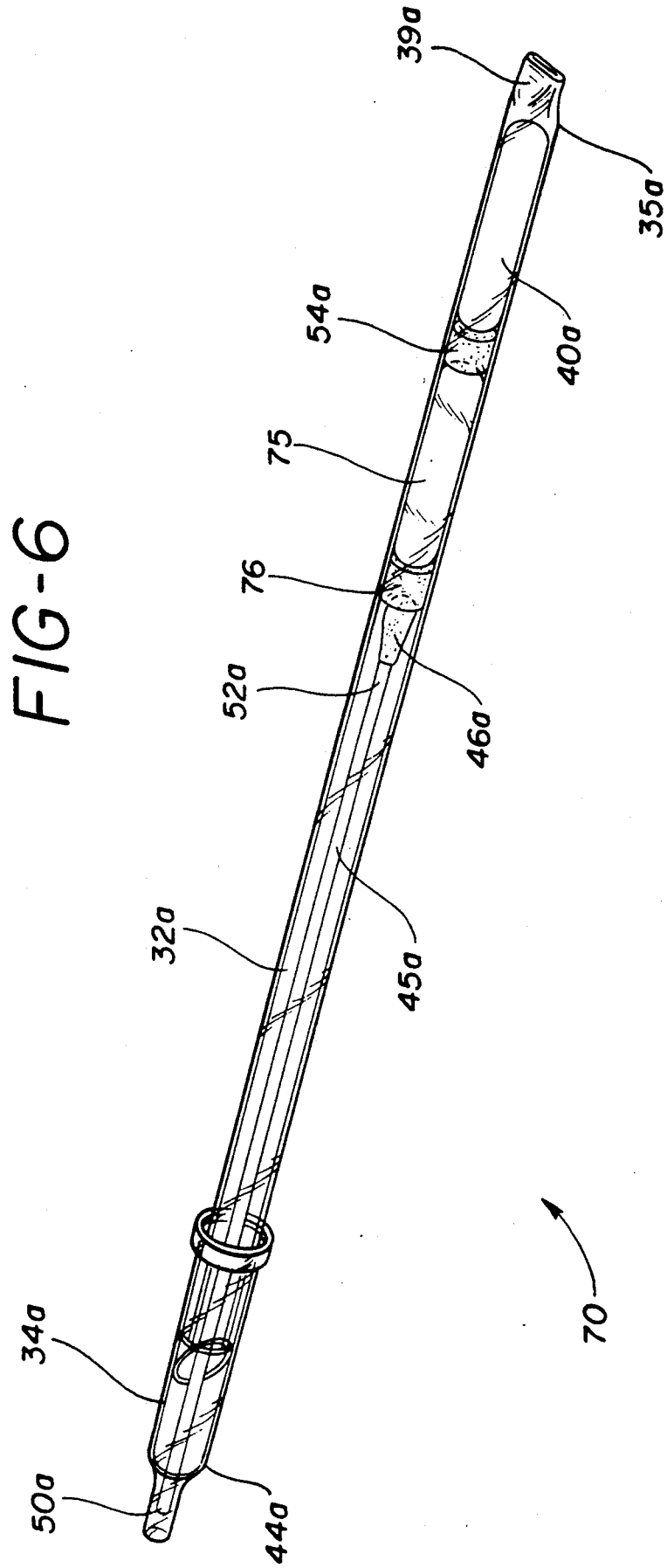
FIG. 6 is a perspective view illustrating a system for collecting and transporting specimens comprising at least two ampoules.

The alternate embodiment of a collecting and transporting system, as shown in, FIG. 6, includes many components of FIGS. 1-5. Accordingly, similar components performing similar functions will be numbered identically to those components of FIGS. 1-5, except that a suffix "a" will be used to identify those similar components in FIG. 6.

FIG. 6 illustrates an alternate embodiment of the invention, collecting and transporting system 70, comprising a sleeve 72 and a collection device 74. In particular, collection device 74 has disposed within the tubular housing adjacent absorbent plug 54a a second frangible ampoule 75. Frangible ampoule 75 preferably holds a test reagent which may be released inside the tubular housing. The test reagent may be used to detect and identify microorganisms and for resleeving detectable antigen in the device.

The test reagent may be one or more of various well known test reagents. The particular test reagent used may be chosen on the basis of the particular type of species being identified. A test reagent such as N,N,N,N tetra methyl-p-phenylenediamine dihydrochloride may be used as disclosed in U.S. Pat. No. 3,876,503 which is hereby incorporated by reference for detecting gonorrhea. Other test reagents such as di-methyl amino-cinnaminaldehyde, beta d galactosidase substrates, gamma glutamylamino peptidase and prolylamine peptidase may also be used as disclosed in U.S. Pat. No. 4,767,702 which is hereby incorporated by reference for detecting specific species of the genus Neisseria. Further test reagents, may include, but are not limited to, hippuric acid for detecting Group B Streptococcus, L-pyrrolidonyl beta naphthylamide and esculin for detecting Group A Streptococcus, acid or mineral acid and sodium nitrite for extracting Group A Streptococcus antigen and tris buffer, sodium chloride, EDTA, sodium azide and N acetyl cysteine for extracting Respiratory Syncytial Virus (RSV) antigen.

Second frangible ampoule 75 is preferably made of, but not limited to the same materials as frangible ampoule 40*a*.

To retain the second frangible ampoule in position and also to restrain flow of released test reagent, a second absorbent plug 76 may be located within the tubular housing. The absorbent plug may be tightly telescoped within the tubular housing and preferably abuts the second frangible ampoule to prevent the latter from sliding.

It will be understood by practitioners in the-art that multiple ampoules may be disposed within the tubular housing of the collection device wherein each ampoule is separated by an absorbent plug. The number of frangible ampoules used is dependent on the need associated with the specimen collected and/or the particular test or immunoassay to be performed.

Various labels and identifying marks, such as bar codes, may be preferably applied to the outer layer surface of the sleeve and the collection device.

The collecting and transporting system may be used for providing viable specimens for in vitro diagnostic testing methods, immunoassays for detecting and identifying microorganisms and for resleeving detectable antigen The system may also be used in clinical situations to resleeve bacteria or other microorganisms from a clinical specimen for inoculation onto or into primary isolation media. The bacteria or microorganisms resleeved by the system may also be used for immunological or DNA/RNA probe testing or other tests to determine the identity and/or antimicrobial susceptibility pattern of the etiological agent.

The tubular member of the sleeve may be made of varying lengths so as to accommodate collection devices that may comprise more than one ampoule to be broken.

The following examples are not limited to any specific embodiment of the invention, but are only exemplary.

EXAMPLE 1

Extraction of Respiratory Syncytial Virus (RSV)

A sampling site is contacted with a swab and a specimen, possibly containing RSV, is removed. The swab is inserted into a collecting and transport device with a tubular housing having two ampoules disposed within. A sleeve is thereafter removably disposed around the housing wherein the ampoules are disposed.

The first ampoule contains a mixture of tris buffer, sodium chloride, EDTA and sodium azide. The second ampoule contains N acetyl cysteine. The first and second ampoules are broken in succession by way of the lever of the sleeve and over a period of minutes, the appropriate RSV antigen is extracted for later testing by an immunological based assay such as DIRECTIGEN 1-2-3® (trademark of Becton, Dickinson and Company, Franklin Lakes, N.J.) sold by Becton, Dickinson Microbiology Systems, Cockeysville, Md.

EXAMPLE 2

Rapid Chromogenic/Colorimetric Test to Identify and Differentiate Group A Streptococcus Strains From Enterococci Strains A sampling site is contacted with a swab and a specimen, possibly containing Group A Streptococcus strains, is removed. The swab is inserted into a collecting and transport device with a tubular housing and two ampoules disposed within. A sleeve is removably disposed around the housing wherein the ampoules are disposed.

The first ampoule contains L-pyrrolidonyl beta-naphthylamide and the second ampoule contains esculin.

The lever of the sleeve exerts pressure onto the tubular housing so that the first ampoule is broken to release the L pyrrolidonyl beta- naphthylamide. If the specimen develops no color, then the test is negative, however, if the specimen turns red, the specimen is positive for Group A Streptococcus.

The second ampoule is then broken by way of the sleeve to release the esculin. If no color develops then the specimen is positive Group A Streptococcus, however, if a blue color develops then the specimen is positive for Enterococci.

EXAMPLE 3

Extraction of Group A Streptococcus Antigen From a Throat Specimen

A throat site is contacted with a swab and a throat specimen, possibly containing Group A Streptococcus is removed. The swab is inserted into a collecting and transporting device with a tubular housing and two ampoules disposed within. A sleeve is removably disposed around the housing wherein the ampoules are disposed.

The first ampoule contains an acid or mineral acid such as acetic acid, citric acid or hydrochloric acid and the second ampoule contains sodium nitrite.

The lever of the sleeve exerts pressure on the tubular housing so that the first and second ampoules are broken in succession to permit the formation of nitrous acid to cause the extraction of Group A Streptococcus antigen if present for further testing by an immunological based assay such as DIRECTIGEN ® Rapid Group A Strep Test (trademark of Becton, Dickinson and Company, Franklin Lakes, N.J.) sold by Becton Dickinson Microbiology Systems, Cockeysville, Md.

EXAMPLE 4

Rapid Presumptive Chromogenic/Colorimetric Test for Neisseria Gonorrhoeae in Male Urethral Discharge A swab is inserted into a collecting and transporting device with a tubular housing two ampoules disposed within. A sleeve is removably disposed around the housing wherein the ampoules are disposed.

The first ampoule contains a saline wetting agent and the second ampoule contains the reagent N,N,N,N tetra methyl p-phenylenediamine di hydrochloride.

The lever of the sleeve exerts pressure onto the tubular housing so that the first ampoule is broken to release the wetting agent onto the swab. The swab is then removed from the device to collect specimen. The swab is reinserted into the device with the collected specimen.

The second ampoule is then broken by way of the sleeve to release the reagent. If *N. gonorrhoeae* is present in the specimen, the reagent will turn purple or blue/-purple.

EXAMPLE 5

Chromogenic Test for Group B Streptococcus Strains

A swab is inserted into a collecting and transporting device with a tubular housing having two ampoules disposed within. A sleeve is removably disposed around the housing wherein the ampoules are disposed.

The first ampoule contains a saline wetting agent and the second ampoule contains hippuric acid.

The lever of the sleeve exerts pressure onto the tubular housing so that the first ampoule is broken to release the wetting agent onto the swab. The swab is then removed from the device to collect specimen and then reinserted into the device with the collected specimen.

The second ampoule is then broken by way of the sleeve to release hippuric acid. If Group B Streptococcus, is present, the specimen will develop a pink color.

EXAMPLE 6

Rapid Chromogenic Constitutive Enzyme Test to Identify and Differentiate Neisseria Meningitidis, Neisseria Gonorrhoeae and Neisseria Lactamica A sampling site is contacted with a swab and a specimen, possibly containing *N. meninqitidis, N. gonorrhoeae* or *N. Lactamica* is removed. The swab is inserted into a collecting and transport device with a tubular housing having four ampoules disposed within. A sleeve capable of surrounding each ampoule when required is removably disposed around the housing wherein the ampoules are disposed.

The first ampoule contains beta d-galactosidase substrate, the second ampoule contains a developer reagent di-methyl amino cinnaminaldehyde, the third ampoule contains gamma-glutamylamine peptidase and the fourth ampoule contains prolylamine peptidase.

The first ampoule is broken by way of the sleeve and if the specimen develops a blue green color, it is positive for *N. lactamica.* If no color develops, then the second and third ampoules are successively broken by way of the sleeve. After the second and third ampoules are broken, if the specimen is positive for *N. meningitidis,* a purple color will develop on the swab. If the specimen is positive for *N. gonorrhoeae* a red color will develop on the swab. If no change in color appears on the swab, then the specimen may be positive for *Branhamella catarrhalis.*

What is claimed is:

1. An apparatus for collecting and transporting biological specimens comprising:

an elongated tubular housing extending from an open end to an opposite closed end;

a specimen collector comprising a cap, a shaft connected to said cap, and a swab connected to an end of said shaft opposite said cap, wherein said shaft and swab are adapted to lie within said tubular housing and said cap closes the open end of said tubular housing;

an ampoule containing a culture sustaining medium disposed within the closed end of said tubular housing;

a plug of absorbent material disposed within said tubular housing between said swab and said ampoule; and a sleeve removably disposed on said closed end of said tubular housing comprising a tubular body member longitudinally extending from an open end to an opposite closed end extremity with a slot at said open end extremity and a lever movably attached to said slot by at least one flexible connection, whereby said lever when actuated provides appropriate pressure to said tubular housing to break said ampoule.

2. The device of claim 1 wherein said ampoule comprises a frangible material.

3. The device of claim 1 wherein said tube and said cap are slidable relative to each other and form a slidable seal.

4. The device of claim 1 further comprising at least a second ampoule positioned within said tube and located adjacent said plug.

5. The device of claim 4 wherein said second ampoule contains a test reagent.

6. The device of claim 1 further comprising a plurality of ampoules disposed within said tube.

7. A method for collecting and transporting biological samples comprising:

(a) providing an apparatus for collecting and transporting biological specimens comprising an elongated tubular housing extending from an open end to an opposite closed end;

a specimen collector comprising a cap, a shaft connected to said cap, and a swab connected to an end of said shaft opposite said cap, wherein said shaft and swab are adapted to lie within said tubular housing and said cap closes the open end of said tubular housing, an ampoule containing a culture sustaining medium disposed within the closed end of said tubular housing;

a plug of absorbent material disposed within said tubular housing between said swab and said ampoule; and a sleeve removably disposed on said closed end of said tubular housing comprising a tubular body member longitudinally extending from an open end to an opposite closed end extremity with a slot at said open open end extremity and a lever movably attached to said slot by at least one flexible connection, whereby said lever when actuated provides appropriate pressure to said tubular housing to break said ampoule.

(b) contacting a sample site with said swab;

(c) obtaining a specimen from said site with said swab;

(d) inserting the swab which contains said specimen into the open end of said housing, (e) closing said housing with said cap to protect said swab and said specimen;

(f) removably attaching said sleeve to the closed end of said housing where said ampoule is housed, and (g) pushing the lever of said sleeve so as to apply a force on said tubular housing which in turn applies a force on said ampoule so that said ampoule breaks and said culture sustaining medium is released in said tubular housing so as to keep said specimen viable.

8. The device of claim 7 wherein said ampoule comprises a test reagent for detecting and identifying microorganisms.

* * * * *